US008557736B2

(12) United States Patent (10) Patent No.: US 8,557,736 B2
Woolard et al. (45) Date of Patent: Oct. 15, 2013

(54) USE OF ABSCISIC ACID TO CONTROL FRUITING

(75) Inventors: Derek D. Woolard, Zion, IL (US); Peter D. Petracek, Grayslake, IL (US); Michael Schroeder, Guggenhausen (DE)

(73) Assignee: Valent BioSciences Corporation, Libertyville, IL (US)

( * ) Notice: Subject to any disclaimer, the term of this patent is extended or adjusted under 35 U.S.C. 154(b) by 852 days.

(21) Appl. No.: 12/011,814

(22) Filed: Jan. 30, 2008

(65) Prior Publication Data

US 2008/0227644 A1 Sep. 18, 2008

Related U.S. Application Data

(60) Provisional application No. 60/898,586, filed on Jan. 31, 2007.

(51) Int. Cl.
*A01N 37/42* (2006.01)
*A01N 37/06* (2006.01)

(52) U.S. Cl.
USPC .............................. 504/171; 504/162; 504/320

(58) Field of Classification Search
USPC ........................................................ 504/320
See application file for complete search history.

(56) References Cited

U.S. PATENT DOCUMENTS

| 4,361,436 | A | 11/1982 | McCarthy et al. | |
| 2005/0198896 | A1* | 9/2005 | Quaghebeur | 47/58.1 FV |
| 2008/0318787 | A1* | 12/2008 | Quaghebeur | 504/142 |

FOREIGN PATENT DOCUMENTS

| JP | 06100407 A | 4/1994 |
| WO | WO 2006018266 A1 * | 2/2006 |

OTHER PUBLICATIONS

JP 06100407, Falling Acceleration of Flowers, or Fruits by Spraying with Natural Type Abscisic Acid and Ethephon, Apr. 12, 1994, Derwent Abstract, pp. 1-2.*
Fruit Thinning Definition, [online]. Britannica Online Encyclopedia, [retrieved on May 14, 2010]. Retrieved from the Internet: <URL:www.britannica.com/EBchecked/topic/592181/thinning>.*
Kamuro Yi, JP 06-100407A, 1994, Internet Translation of Japanese Patent cited on Information Disclosure Statement dated Jul. 25, 2008, pp. 1-3.*
Analog Definition. 1994, Webster's II New Riverside University Dictionary, 3 pages.*
Reighard, Gregory L., Peach Thinning, 1987, Peach Production Handbook, University of Georgia Extension Services, 5 pages.*
Kende et al., "The five 'classical' plant hormones", The Plant Cell, Jul. 1997, vol. 9, pp. 1197-1210.
Milborrow, "Inhibitors", Advanced Plant Physiology, pp. 76-110.
EP Search Report issued Sep. 28, 2011.
Delvalle et al., "Thinning of peaches *Prunus-persica* by temporary inhibition of photosynthesis with terbacil", Journal of the American Society for Horticultural Science, American Society for Horticultural Science, Alexandria, VA US, vol. 110, No. 6, Jan. 1, 1985, pp. 804-807, XP009152252.
Schneider et al., "Studied on the mechanism of fruit abscission in apple and peach", Journal of the American Society for Horticultural Science, American Society for Horticultural Science, Alexandria, VA, US, vol. 102, No. 2, Jan. 1, 1997, pp. 179-181, XP009152253.

* cited by examiner

*Primary Examiner* — John Pak
*Assistant Examiner* — Andriae M Holt
(74) *Attorney, Agent, or Firm* — Wood, Phillips, Katz, Clark & Mortimer

(57) ABSTRACT

The present invention is directed to the treatment of a plant at the flowering or fruiting stage to reduce the number of fruits that the plant sets and grows to maturity with an effective amount of abscisic acid or its salts, derivatives or analogs.

7 Claims, No Drawings

USE OF ABSCISIC ACID TO CONTROL FRUITING

FIELD OF THE INVENTION

This invention relates to a novel method for reducing the number of fruits on plants by treating the plants with abscisic acid (ABA). Specifically, the invention relates to a method for reducing the crop load of plants.

BACKGROUND OF THE INVENTION

Many plants set more fruits than is desirable for the production of high quality fruit of commercial size. Plants setting too many fruits can lead to each fruit being smaller than if the fruit set is reduced, by a process called thinning.

Thinning of fruits, or the flowers that can become fruits, can be accomplished by hand removal of small fruits or flowers by hand thinning. Hand thinning is very costly and labor to complete the job can be difficult to obtain.

Chemical treatments have been used to commercially thin a variety of crops including apples and grapes. There are currently no effective chemical fruitlet thinners for stone fruit. Chemical thinners are sometimes not effective due to under thinning, over thinning, chemical burns due to phytotoxicity/, inhibition of fruit growth and abscission of leaves. For example, a chemical thinner that induces indiscriminate abscission of leaves and fruit would be of no commercial value. Consequently, there is a need for improved chemical thinning agents.

ABA is a naturally-occurring hormone found in all higher plants (Cutler and Krochko, 1999, Trends in Plant Science, 4:472-478; Finkelstein and Rock, 2002. The *Arabidopsis* Book. ASPB, Monona, Md., 1-52). Endogenous ABA is involved in a number of physiological processes including modulation of germination, dormancy, stomatal conductance, plant growth and leaf abscission (Milborrow, 1984, in Plant Physiology, ed Wilkins, 76-110; Kende and Zeevaart, 1997, Plant Cell, 9:1197-1210).

Quaghebeur (2005, US Patent Application No. 2005/0198896 A1) speculated that ABA causes defoliation, bloom inhibition, and fruit drop and induces hibernation-like states. The uses for ABA on fruit trees described in Quaghebeur (2005) are limited to enhancing leaf removal, reducing cherry cracking and reducing burgeoning growth caused by rain. When using ABA on apple and pear according to Quaghebeur (2005), quick leaf abortion is observed and airflow through the tree is improved. However, Quaghebeur (2005) does not mention the selective removal of flowers or young fruitlets preferentially over leaf defoliation and does not suggest the use of ABA as an effective thinning agent.

There are no published reports on the use of ABA as a thinning agent.

Our studies have shown that ABA applied at or shortly after bloom is an effective fruit thinner without causing unacceptable levels of leaf drop. Surprisingly, our studies have also shown that spraying fruit trees with ABA during bloom or shortly after bloom does not lead to fruit growth inhibition or a hibernation-like state, but rather to enhanced fruit growth compared to untreated trees.

SUMMARY OF THE INVENTION

The present invention is directed to the treatment of a stone fruit plant at the flowering or fruiting stage with an effective amount of ABA or its salts or derivatives or analogs to reduce the number of fruits that the plant sets and grows to maturity. More specifically, the invention relates to a method for applying to flowering or fruiting plants an effective amount of abscisic acid or its salts or its derivatives or analogs to reduce the number of fruits that set and mature on the plant.

DETAILED DESCRIPTION

As used herein the term "ABA" refers to abscisic acid (S-ABA; ABA; S-(+)-abscisic acid; +-ABA, (+)-(S)-cis, trans-abscisic acid, (+)-(S)-cis trans-ABA; S-ABA; (S)-5-(1-hydroxy-2,6,6,-trimethyl-4-oxo-2-cyclohexen-1-yl)-3-methyl-(2Z,4E)-pentadienoic acid; CAS registry no. [21293-29-8]).

As used herein, the term "salt" refers to the water soluble salts of ABA or ABA analogs or derivatives, as appropriate. Representative such salts include inorganic salts such as the ammonium, lithium, sodium, potassium, magnesium and calcium salts and organic amine salts such as the triethanolamine, dimethylethanolamine and ethanolamine salts.

Presently preferred ABA analogs and derivatives include PBI-429, PBI-524, PBI-696 and PBI-702.

For the purposes of this Application, abscisic acid analogs are defined by Structures 1, 2 and 3, wherein for Structure 1:

the bond at the 2-position of the side chain is a cis- or trans- double bond, the bond at the 4-position of the side chain is a trans- double bond or a triple bond, the stereochemistry of the alcoholic hydroxyl group is S-, R- or an R,S-mixture, the stereochemistry of the R1 group is in a cis- relationship to the alcoholic hydroxyl group, R1=ethynyl, ethenyl, cyclopropyl or trifluoromethyl, and R2=hydrogen or lower alkyl

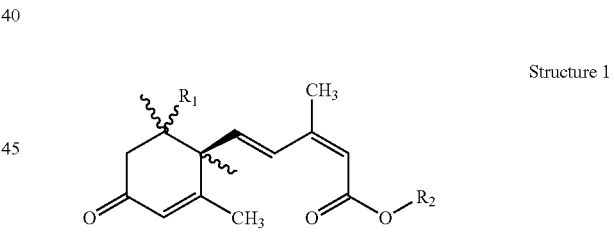

Structure 1 wherein lower alkyl is defined as an alkyl group containing 1 to 4 carbon atoms in a straight or branched chain, which may comprise zero or one ring or double bond when 3 or more carbon atoms are present.

For PBI-429, R1 is ethynyl and R2 is a methyl group.

For PBI-524, R1 is ethynyl and R2 is a hydrogen.

For PBI-696, R1 is cyclopropyl and R2 is a methyl group.

For Structure 2:

the bond at the 2-position of the side chain is a cis- or trans- double bond, the bond at the 4-position of the side chain is a triple bond, the stereochemistry of the alcoholic hydroxyl group is S-, R- or an R,S- mixture, R1=hydrogen or lower alkyl

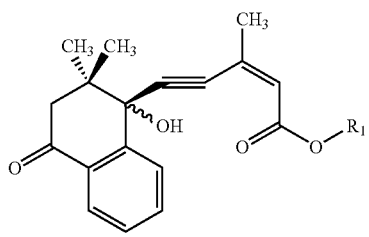

Structure 2 wherein lower alkyl is defined as an alkyl group containing 1 to 4 carbon atoms in a straight or branched chain, which may comprise zero or one ring or double bond when 3 or more carbon atoms are present.

For PBI-702, R1 is a methyl group.
For Structure 3:
the bond at the 2-position of the side chain is a cis- or trans- double bond,
the bond at the 4-position of the side chain is a trans- double bond,
the stereochemistry of the alcoholic hydroxyl group is S-, R- or an R,S- mixture,
R1=hydrogen or lower alkyl Structure 3 wherein lower alkyl is defined as an alkyl group containing 1 to 4 carbon atoms in a straight or branched chain, which may comprise zero or one ring or double bond when 3 or more carbon atoms are present.

It is also contemplated that salts of the ABA analogs set forth above may be utilized in accordance with the present invention.

The applied concentration of ABA, its salts, derivatives or analogs can vary widely depending on the water volume applied to plants as well as other factors such as the plant age and size, and plant sensitivity to ABA, but is generally in the range of about 1 ppm to about 10,000 ppm, preferably from about 10 to about 2000 ppm, and more preferably about 50 to about 1000 ppm.

Other ingredients such as surfactants can be utilized in compositions useful in the present invention.

The presently preferred surfactant for ABA performance is Brij 98 (polyoxyethylene (20) oleyl ether) available from Uniqema (Castle, Del.). Other surfactants are also useful in the present invention, including but not limited to: other surfactants in Brij family (polyoxyethylene fatty alcohol ether) from Uniqema (Castle, Del.); surfactants in Tween family (Polyoxyethylene sorbitan esters) from Uniqema (Castle, Del.); Silwet family (Organosilicone) from Union Carbide (Lisle, Ill.); Triton family (Octylphenol ethoxylate) from The Dow Chemical Company (Midland, Mich.); Tomadol family (ethoxylated linear alcohol) from Tomah3 Products, Inc. (Milton, Wis.); Myrj family (Polyoxyethylene (POE) fatty acid esters) from Uniqema (Castle, Del.); Span family (Sorbitan ester) from Uniqema (Castle, Del.); and Trylox family (Ethoxylated Sorbitol and Ethoxylated Sorbitol Esters) from Cognis Corporation (Cincinnati, Ohio); as well as commercial surfactant Latron B-1956 (77.0% modified phthalic/glycerol alkyl resin and 23.0% Butyl alcohol) from Rohm & Haas (Philadelphia, Pa.); Caspil (Blend of Polyether-polymethylsiloxanecopolymer and nonionic surfactant) from Aquatrols (Paulsboro, N.J.); Agral 90 (Nonyl phenol ethoxylate) from Norac Concept. Inc. (Orleans, Ontario, Canada); Kinetic (99.00% Proprietary blend of polyalkyleneoxide modified polydimethylsiloxane and nonionic surfactants) from Setre Chemical Company (Memphis, Tenn.); and Regulaid (90.6% 2-butoxyethanol, poloxalene, monopropylene glycol) from KALO, Inc. (Overland Park, Kans.).

Plants that can be treated in accordance with the present invention are woody angiosperm plants, preferably stone fruits, as for example peaches, plums and apricots.

The invention may be illustrated by the following representative, non-limiting examples.

EXAMPLE 1

Limbs of PF-27 peach trees with fruit at the shuck split stage were flagged; the number of fruit distal to the flagging was counted. The limbs were sprayed to runoff with either water or 1000 ppm abscisic acid (S-ABA; ABA; S-(+)-abscisic acid; +-ABA, (+)-(S)-cis,trans-abscisic acid,(+)-(S)-cis, trans-ABA; S-ABA; (S)-5-(1-hydroxy-2,6,6,-trimethyl-4-oxo-2-cyclohexen-1-yl)-3-methyl-(2Z,4E)-pentadienoic acid; CAS no. 21293-29-8). After 8 and 19 days the fruit were re-counted and the percent fruit retention was determined. Limbs treated with 1000 ppm ABA retained less fruit than limbs treated with water 19 days following treatment (Table 1).

TABLE 1

Effect of foliar spray with ABA on fruit retention on peach tree limbs.

| Treatment | Days after treatment | |
|---|---|---|
| | 8 days after treatment | 19 days after treatment |
| Control | 99% | 86% |
| 1000 ppm ABA | 97% | 69% | n = 1 limb per tree on each of 10 trees

EXAMPLE 2

Trees of Cacaks Schone plum and Katinka plum were sprayed with 600 ppm ABA at the fruitlet set stage or left untreated. The number of fruit per flower was determined after the normal fruit drop period had ended. At harvest the weight per 100 fruits was measured for both the ABA treated and the untreated trees. Spraying Cacaks Schone or Katinka plum trees with ABA at the fruitlet set stage reduced the number of fruits per flower and increased the average fruit weight compared to untreated trees (Table 2).

TABLE 2

Effect of ABA on fruit set and fruit size of plums.

| | Variety | | | |
|---|---|---|---|---|
| | Cacaks Schone | | Katinka | |
| Treatment | Fruit/flower | 100 fruit weight (kg) | Fruit/flower | 100 fruit weight (kg) |
| Untreated | 0.18 | 1.88 | 0.57 | 1.68 |
| 600 ppm ABA | 0.09 | 2.23 | 0.45 | 2.35 |

EXAMPLE 3

Trees of Cacaks plum were sprayed at petal fall (BBCH stage 69) with 500 ppm or 1000 ppm ABA or left untreated (Table 3). Percent fruit set, average yield and average fruit weight were determined at harvest. Spraying Cacaks plum trees with ABA reduced fruit set percentage and yield per tree and increased average fruit weight (Table 3).

TABLE 3

Effect of application of ABA to Cacaks plum at petal fall (BBCH stage 69).

| Treatments | % Fruit set | Yield (kg/tree) | Fruit weight (g) |
|---|---|---|---|
| Untreated | 29 | 10.7 | 13.6 |
| 500 ppm ABA | 20 | 8.0 | 14.5 |
| 1000 ppm ABA | 11 | 7.0 | 14.6 |

EXAMPLE 4

Trees of Katinka plum were sprayed at petal fall (BBCH stage 69) with 500 ppm or 1000 ppm ABA or left untreated (Table 4). Percent fruit set, average yield and average fruit weight were determined at harvest. Spraying Katinka plum trees with ABA reduced fruit set percentage and yield per tree and increased average fruit weight (Table 4).

TABLE 4

Effect of application of ABA to Katinka plum at petal fall (BBCH stage 69).

| Treatments | % Fruit set | Yield (kg/tree) | Fruit weight (g) |
|---|---|---|---|
| Untreated | 47 | 7.8 | 24.7 |
| 500 ppm ABA | 28 | 4.2 | 26.2 |
| 1000 ppm ABA | 21 | 4.4 | 28.0 |

EXAMPLE 5

Apricot and peach trees were sprayed at petal fall (BBCH stage 69) with 1000 ppm ABA or left untreated (Table 5). Percent fruit set was determined at harvest. Spraying apricot and peach trees with ABA reduced percent fruit set (Table 5).

TABLE 5

Effect of application of ABA to Apricot and Peach at petal fall (BBCH stage 69).

| | % Fruit set | |
|---|---|---|
| Treatments | Apricot | Peach |
| Untreated | 39 | 74 |
| 1000 ppm ABA | 33 | 36 |

EXAMPLE 6

European seedless cucumber (var. *Flamingo*) plants were grown in a greenhouse. At the 20 node growth stage the plants were sprayed to drip with ABA (100 ppm) solution or left unsprayed (control). ABA treated plants had twice the rate of fruit abortion compared to the control plants (Table 6). This Example shows that ABA can selectively reduce crop load without inducing fruit abscission.

TABLE 6

Effect of foliar sprays with ABA on abortion of cucumber fruits.

| Treatment | Percentage of basal 18 cucumber fruits per plant that aborted |
|---|---|
| Control | 34 |
| ABA | 68 |

* n = 5 replicate plants per treatment.

The invention claimed is:
1. A method of thinning fruit from peach, plum, or apricot trees comprising applying about 500 ppm to about 1000 ppm of abscisic acid (ABA) and/or salts thereof to a peach, plum, or apricot tree during its flowering stage, petal stage, shuck split stage, or fruitlet set stage of growth, wherein the number of fruits that set and mature on said tree is reduced and average fruit weight on said tree is increased.
2. The method of claim 1 wherein the tree is a peach tree.
3. The method of claim 1 wherein the tree is a plum tree.
4. The method of claim 1 wherein the tree is an apricot tree.
5. The method of claim 1 wherein the amount of ABA and/or salts thereof is about 500 ppm.
6. The method of claim 1 wherein the amount of ABA and/or salts thereof is about 600 ppm.
7. The method of claim 1 wherein the amount of ABA and/or salts thereof is about 1000 ppm.

* * * * *